United States Patent
Mention

(10) Patent No.: US 6,274,172 B1
(45) Date of Patent: Aug. 14, 2001

(54) THERAPEUTIC EFFERVESCENT COMPOSITIONS

(75) Inventor: Jacky Andre Gustave Mention, Leognon (FR)

(73) Assignee: SmithKline Beecham Laboratoires Pharmaceutiques, Nanterre Cedex (FR)

(*) Notice: Subject to any disclaimer, the term of this patent is extended or adjusted under 35 U.S.C. 154(b) by 0 days.

(21) Appl. No.: 08/981,227

(22) PCT Filed: Jun. 28, 1996

(86) PCT No.: PCT/EP96/02934
  § 371 Date: Sep. 3, 1998
  § 102(e) Date: Sep. 3, 1998

(87) PCT Pub. No.: WO97/02014
  PCT Pub. Date: Jan. 23, 1997

(51) Int. Cl.⁷ .............. A61K 9/14; A61K 9/16; A61K 9/20; A61K 9/46
(52) U.S. Cl. ............ 424/466; 424/464; 424/465; 424/489; 514/784; 514/951
(58) Field of Search .................. 424/466, 465, 424/489, 464

(56) References Cited

U.S. PATENT DOCUMENTS 5,468,504 * 11/1995 Schaeffer .............. 424/466
5,814,337 * 9/1998 Merrifield et al. ......... 424/466

FOREIGN PATENT DOCUMENTS 0 186 090 A3  12/1985 (EP).
0 233 853 A1  1/1987 (EP).
0 265 951 A3  10/1987 (EP).
0 414 115 A1  8/1990 (EP).

* cited by examiner

Primary Examiner—James M. Spear
(74) Attorney, Agent, or Firm—Dara L. Dinner; Stephen Venetianer; Charles M. Kinzig

(57) ABSTRACT

Granulates comprising an effervescent couple of anhydrous powdered monosodium citrate and powdered sodium bicarbonate and prepared using a roller compactor are formulated into pharmaceutical compositions.

21 Claims, No Drawings

THERAPEUTIC EFFERVESCENT COMPOSITIONS

This application is a 371 of PCT/EP96/02934 filed Jun. 28, 1996.

This invention relates to novel granulates comprising effervescent couples, pharmaceutical formulations comprising such granulates, to processes for the manufacture thereof and the use of such formulations in therapy.

Effervescent pharmaceutical formulations are well known in the art. At the simplest level, such compositions include a couple which comprises an acid such as citric acid or a mono or dihydrogen salt thereof and a carbon dioxide source such as a carbonate or hydrogen carbonate alkali metal salt, such as sodium hydrogen carbonate. These do not react together when dry but combine to release carbon dioxide and an effervescent effect in the presence of water. The pharmaceutical compositions may be in the form of a tablet for dissolving in water or a dispersible powder for sprinkling onto water, prior to administration. The components of the couple are blended together during manufacture of the composition. It is important to avoid water, to prevent premature effervescence. The latter, in the case of a citric acid or mono hydrogen salt/sodium hydrogen carbonate couple, leads to the formation of carbon dioxide and may lead to additional and undesirable degradation when the drug substance is acid sensitive.

A suitable drug for use in an effervescent formulation is cimetidine, marketed by Smith Kline & French Laboratories as Tagamet. An effervescent tablet preparation containing 200 mg cimetidine and a citric acid/sodium hydrogen carbonate stoichiometric couple is marketed in several European countries. The couple is produced by a wet granulation process. The effervescent formulation also helps to overcome the bitter taste of cimetidine. In addition. EP 0 233 853-A (Laboratoires Smith Kline & French) describes effervescent couples particularly suitable for use with $H_2$ antagonists such as cimetidine which are sensitive to acid. The couple comprises a mixture of mono- and dialkali metal citrate salts in a defined ratio. This is prepared by partially neutralising citric acid by treatment thereof with an alkali metal carbonate or bicarbonate salt in water and stopping the reaction when a certain amount of carbon dioxide has been evolved. This processes involves several steps, including wet granulation and subsequent drying. A shorter, more efficient process would be commercially attractive.

We have now found that improved couples may be prepared more efficiently if a dry Granulation technique involving a roller compactor is used to blend together the components of the couple. The use of a roller compactor is becoming increasingly common in pharmaceutical technology. The technique depends upon the densification of a fine powder to obtain fragments or flakes of undefined shape. These flakes are then usually crushed to obtain granulates which are screened to the size required by the user.

The use of roller compaction to prepare granulates comprising a sodium hydrogen sulphate/sodium hydrogen carbonate couple, for subsequent incorporation into effervescent tablets for use in cleaning toilet bowls, is described in Pharmaceutical Dosage Forms: Tablets, vol 1, ed H A Lieberman and L Lachman (Marcel Dekkel, 1980).

Accordingly, the present invention provides for pharmaceutical granulates comprising an effervescent couple, characterised in that the couple comprises anhydrous powdered monosodium citrate and powdered sodium bicarbonate and the granulates are prepared using a roller compactor.

Such granulates are found to dissolve more quickly and more fully in water and there is also no chemical reaction between the components.

The most effective granulates are made using anhydrous powdered monosodium citrate of a certain particle size range. Suitable grades of anhydrous powdered monosodium citrate comprise particles which are substantially (i.e. about more than 90%) within the range 0 to 500 microns, preferably 355 microns, more preferably 0 to 250 microns. Suitable grades are available from Roche (monosodium citrate anhydrous powder, maximum of 5% w/w with grain size >0.250 mm), Boehringer Ingelheim (monosodium zilrate wasserfrei Art-Nr 661 511, minimum of 90% w/w with grain size <0.150 mm), Jungbunzlauer (maximum of 5% w/w with grain size >0.355 mm) and Haarmann & Reimer Corp. (maximum of 1% with grain size >0.500 mm).

Suitable grades of powdered sodium bicarbonate comprise particles which are substantially (i.e. about more than 90%) within the range of 0 to 500 microns, preferably 270 microns more preferably 0 to 130 microns. Suitable grades of powdered sodium bicarbonate are available from Solvay, for instance the grades 0 to 13 (particle size, by sieving method: >0.16 mm max; 15 g/kg) and extra-fine (particle size by sieving method: >0.125 mm max; 20 g/kg).

Tablets manufactured using Granulates with low particle size were found to be harder than those manufactured using granulates with large particle size but were otherwise comparable.

Granulates according to the present invention may be obtained by a process which comprises the steps of:
a) blending together the components of the couple;
b) roller compacting the blend to produce flakes;
c) crushing the flakes to obtain granulates; and
d) if desired, screening the granulates by size.

Suitably, the components of the couple are blended together at a controlled temperature, for instance about 20° C. and controlled relative humidity, for instance about 20% RH and processed in a roller compactor to form flakes. Roller compaction may be carried out over a range of linear compaction strengths, the appropriate value being influenced by the particle size of the monosodium citrate and sodium hydrogen carbonate. For smaller particle sizes (for instance, the grades of monosodium citrate from Boehringer Ingelheim and sodium hydrogen carbonate from Solvay previously mentioned), linear roller compaction strengths of about 20 KN/cm are found to give suitable granulates for further processing into final finished forms such as tablets. For larger particle sizes (for instance monosodium citrate from Jungbunzlauer), linear compaction strengths of about 30 KN/cm are preferred. The flakes thus obtained are then crushed to obtain granulates which are screened to the size required for further processing, suitably a size in the range 0 to 1250 microns is used. Suitably the granulates thus obtained are calibrated for effervescent potency using a standard assay, prior to further use.

Suitably, granulates according to the present invention are incorporated into a pharmaceutical formulation. Accordingly, in a further aspect, the present invention provides a pharmaceutical formulation comprising granulates comprising an effervescent couple and a drug substance which may optionally be incorporated into the Granulates, characterised in that the couple comprises anhydrous powdered monosodium citrate and powdered sodium bicarbonate and the granulates are processed using a roller compactor.

Suitably, granulates may comprise the components of the couple and, optionally, other pharmaceutically acceptable excipients and/or drug substance. Accordingly, in a further aspect, the present invention provides pharmaceutical formulations comprising Granulates comprising an effervescent couple and a drug substance, characterised in that the couple comprises anhydrous powdered monosodium citrate and powdered sodium bicarbonate and the granulates are prepared using a roller compactor.

Suitable drug substances include $H_2$-antagonists well known in the art such as ranitidine, cimetidine, famotidine, nizatidine and roxatine or pharmaceutically acceptable salts thereof. A representative drug substance is cimetidine or the hydrochloride salt thereof. Other suitable drug substances include those obtainable directly 'over the counter' (OTC drugs) such as analgesics, for instance aspirin, ketoprofen, naproxen, paracetamol and ibuprofen. Other suitable products in which such effervescent couples may be incorporated include indigestion products, vitamin supplements and antibiotics.

Suitably, the drug substance is incorporated in an amount such that individual tablets comprise unit dosages of the particular medicament, for instance 200 mg of cimetidine or 500 mg of paracetamol.

Suitable pharmaceutical formulations include effervescent tablets and sachets containing water dispersible powders. Pharmaceutical formulations according to the present invention may be prepared by lending together the granulates formed by roller compaction with other components prior to processing into final form. Roller compaction may also be extended to include other components, such as drug substance and excipients such as lubricants, disintegrants, flavours and sweeteners. For tablets, final processing may include compressing into tablets using a tabletting machine.

Preferably, monosodium citrate and sodium bicarbonate, as herein before defined, are blended together and then roller compacted, preferably in the absence of water, to form flakes which are then crushed to give granulates. The granulates thus obtained may then be combined with druo substance, for instance cimetidine (or the hydrochloride salt thereof), conventional tabletting or filling agents and, optionally, sweeteners, flavours and lubricants and compressed or filled together, suitably under controlled ambient conditions, to form tablets or sachets, respectively. Suitable tablets will have a hardness in the range 6 to 12 Kp. The hardness of the final tablets is found to be influenced by the linear roller compaction strength used in preparing the granulates. Suitable linear compaction strengths are in turn influenced by the particle size of the monosodium hydrogen carbonate and sodium hvdrogen carbonate. For smaller particle sizes (for instance the grades of monosodium citrate from Boehringer Ingelheim and sodium hydrogen carbonate from Solvay previously mentioned) a linear roller compaction strength of about 20 KN/cm is preferred. Higher linear compaction strengths are found to granulates which when incorporated into tablets give harder tablets (up to 17 Kp). At a linear compaction strength of less than 16 KN/cm, subsequent tablets are found to be very soft. For larger particle sizes (for instance monosodium citrate from Jungbunzlauer), a linear compaction strenoth of about 30 KN/cm is preferred. Tablets comprising cimetidine show no cimetidine degradation problems after storage for 2 months at 40° C.

In addition, drug substance, for instance cimetidine, may also be blended together with the components of the couple and the mixture then subjected to roller compaction, followed by crushing to give granulates. These granulates may then be blended together with sweeteners, flavours and lubricants and then compressed into tablets. The sweeteners and flavours may also be incorporated into the initial blend, for roller compaction.

Suitable sweeteners are well known in the art and include aspartame, sodium saccharin, acesulfame potassium and sodium cyclamate.

Suitable lubricants are well known in the art and include PEG 6000, sodium benzoate and dimethicone.

The formulations of the present invention may also include additional excipients and agents well known in the art, for instance disintegrants, wetting agents and colouring agents.

Pharmaceutical formulations according to the present invention are of use in therapy according to the identity of the drug substance contained therein. Accordingly, in a further aspect, the present invention provides for a pharmaceutical formulation herein before defined for use in therapy. The present invention also provides for the use of a couple as herein before defined in the manufacture of a medicament for use in therapy. Such pharmaceutical formulations containing an $H_2$-antagonist such as cimetidine are of use in the treatment of duodenal, gastric, recurrent and stomach ulcerating reflux oesophagitis, and in the management of patients who are at high risk from haemorrhage of the upper gastro-intestinal tract.

The invention will now be illustrated by the following example.

EXAMPLE 1

'200 mg' effervescent tablet comprising cimetidine

1. Stoichiometric Roller Compacted Effervescent Granules

| | |
|---|---|
| Anhydrous powdered monosodium citrate (ex B Ingelheim) | 1426.2g |
| Powdered Sodium bicarbonate (ex Solvay) | 1118.8 |

The ingredients were blended to-ether and subjected to roller compaction at a linear compaction strength of 20 KN/cm at 20–25° C. and about 20%RH. The flakes were then crushed and size-sorted by sieving to give granulates for use in tablet formulation.

2. Tablet

| | w/w |
|---|---|
| Stoichiometric roller compacted effervescent granulates | 2,545 g |
| Cimetidine base | 200.0 |
| Flavours | 27.5 |
| Aspartame | 15.0 |
| Saccharin Sodium | 8.0 |
| PEG 6000 | 20.0 |
| Sodium benzoate | 100.0 |

The above ingredients, suitably scaled up, were blended together in a mixing device at 20–25° C. and about 20% RH and the resultant blend tabletted on a rotative press fitted with 22 mm punches. This gave flat round tablets weighing 2915.5 mg with a hardness about 6 to 12 Kp which dissolved in 45 to 75 s in water at 20° C.

EXAMPLE 2

'500 mg' effervescent tablet comprising paracetamol

1. Stoichiometric Roller Compacted Effervescent Granules

| | |
|---|---|
| Anhydrous powdered monosodium citrate (ex Jungbunzlauer) | 1426.2g |
| Powdered sodium bicarbonate 0/13 (ex Solvay) | 1118.8 |

The ingredient were blended together and subjected to roller compaction at a linear compaction strength of 30

KN/cm at 20–25° C. and about 20% RH. The flakes were then crushed and size-sorted by sieving through a 1.25 mm screen to give granulates for use in tablet formulation.

2. Tablet

|  | (w/w) |
|---|---|
| Stoichiometric roller compacted effervescent granules | 1840.0 mg |
| Paracetamol (powdered) | 500.0 mg |
| Sorbitol | 400.0 mg |
| PEG 6000 | 100.0 mg |
| Polysorbate 80 | 3.0 mg |
| Sodium saccharinate | 8.0 mg |
| (TOTAL | 2851.0 mg) |

The polysorbate was mixed with a part of sorbitol to give an homogeneous dry mixing.

After the above mixing, the remaining sorbitol and other components were blended together in a mixing device at 20–25° C. and about 20% RH. The resultant blend was tabletted on a press fitted with 20mm punches.

The tablets obtained showed following characteristics:

| weight | 2851 mg |
|---|---|
| thickness | about 4.48 mm |
| dissolution time | about 45 s |

What is claimed is:

1. A process for preparing pharmaceutical granulates comprising an effervescent couple which process comprises the steps of:
   a) blending together the components of the couple, which are anhydrous powdered monosodium citrate and powdered sodium bicarbonate;
   b) roller compacting the blend to produce flakes;
   c) crushing the flakes to obtain granulates; and
   d) if necessary and so desired, screening the granulates by size.

2. The pharmaceutical granulates produced according to claim 1 which further comprise a drug substance incorporated into the granulates.

3. The pharmaceutical granulates produced according to claim 1 in which the anhydrous powdered monosodium citrate particles used are substantially within the size range less than 500 microns.

4. The pharmaceutical granulates produced according to claim 3 in which the anhydrous powdered monosodium citrate particles used are substantially within the size range less than 355 microns.

5. The pharmaceutical granulates produced according to claim 4 in which the anhydrous powdered monosodium citrate particles used are substantially within the size range less than 250 microns.

6. The pharmaceutical granulates produced according to claim 1 in which the powdered sodium bicarbonate particles used are substantially within the size range less than 500 microns.

7. The pharmaceutical granulates produced according to claim 6 in which the powdered sodium bicarbonate particles used are substantially within the size range less than 270 microns.

8. The pharmaceutical granulates produced according to claim 7 in which the powdered sodium bicarbonate particles used are substantially within the size range less than 130 microns.

9. The pharmaceutical granulates produced according to claim 2 in which the drug substance in an $H_2$-antagonist or an analgesic.

10. A pharmaceutical formulation comprising granulates which comprise an effervescent couple, and a drug substance incorporated into the granulates, in which the couple comprises anhydrous powdered monosodium citrate and powdered sodium bicarbonate; and wherein the drug substance is cimetidine, or the hydrochloride salt thereof, or paracetamol, and wherein the granulates are prepared using a roller compactor.

11. The pharmaceutical granulates according to claim 2 which are further compressed into a tablet or further formulated as a water dispersible powder.

12. A process for preparing pharmaceutical granulates which granulates comprising an effervescent couple and a drug substance, and wherein the couple comprises anhydrous powdered monosodium citrate, and powdered sodium bicarbonate, which process comprises the steps of:
   a) blending together the components of the couple;
   b) roller compacting the blend to produce flakes;
   c) crushing the flakes to obtain granulates; and
   d) if necessary and so desired, screening the granulates by size;
   e) adding to the flakes of step (c) or (d) a drug substance.

13. The pharmaceutical formulation according to claim 10 wherein the cimetidine or hydrochloride salt thereof is incorporated in to the granulates after the effervescent couple has been roller compacted.

14. The pharmaceutical granulates according to claim 2 wherein the drug substance is incorporated into the granules after the effervescent couple has been roller compacted.

15. A pharmaceutical formulation according to claim 9 in the form of a tablet or a water dispersible powder.

16. The process according to claim 12, which process further comprises admixing the components of step (a), the granulates of step (c) or step (e) with additional excipients.

17. The process according to claim 16 wherein the drug substance is an $H_2$-antagonist or an analgesic.

18. The process according to claim 17 wherein the $H_2$-antagonist is cimetidine, or the hydrochloride salt thereof, and the analgesic is paracetamol.

19. The process according to claim 16 wherein the granulates have particles which are substantially less than 500 microns in size.

20. The process according to claim 19 wherein the granulates have particles which are substantially less than 270 microns in size.

21. A pharmaceutical formulation comprising granulates according to claim 16, in the form of a tablet or sachet.

* * * * *